United States Patent
Nibhanipudi

(10) Patent No.: US 9,777,310 B2
(45) Date of Patent: Oct. 3, 2017

(54) LEUKOCYTE ESTERASE DETECTION FROM THROAT SWAB

(71) Applicant: Kumara Venkatanarayana Nibhanipudi, Hyderabad (IN)

(72) Inventor: Kumara Venkatanarayana Nibhanipudi, Hyderabad (IN)

( * ) Notice: Subject to any disclaimer, the term of this patent is extended or adjusted under 35 U.S.C. 154(b) by 0 days.

(21) Appl. No.: 14/980,552

(22) Filed: Dec. 28, 2015

(65) Prior Publication Data
US 2016/0194682 A1 Jul. 7, 2016

(30) Foreign Application Priority Data
Jan. 2, 2015 (IN) .............................. 33/CHE/2015

(51) Int. Cl.
*C12Q 1/44* (2006.01)
(52) U.S. Cl.
CPC ........... *C12Q 1/44* (2013.01); *C12Q 2334/70* (2013.01)
(58) Field of Classification Search
None
See application file for complete search history.

(56) References Cited

U.S. PATENT DOCUMENTS 7,316,910 B2 * 1/2008 Mosher ................... C12Q 1/37
424/165.1
2009/0325276 A1 * 12/2009 Battrell ............... B01F 11/0071
435/287.2

OTHER PUBLICATIONS

Liu M. et al. Group I *Streptococcus* Secreted Esterase Hydrolyzes Platelet Activating Factor to Impede Neutrophil Recruitment and Facilitate Innate Immune Evasion. PLoS Pathogens 8(4)1-5, Apr. 2012.*
DeLozier J. et al. The Leukocyte Esterase Test for Detection of Cerebrospinal Fluid Leukocytosis and Bacterial Meningitis. Annals of Emergency Medicine 18(11)1191-8, Nov. 1989.*
Blum R. et al. Detection of Pyuria and Bacteriuria in Symptomatic Ambulatory Women. Gen Internal Medicine 7:140-144, 1992.*
Behrman et al. "Group A Streptococci", Nelson Textbook of Pediatrics, 13th edition, 1987, pp. 577-578.
Farahmand, F. et al. "Diagnosis of spontaneous bacterial peritonitis in children by reagent strip", Acta Medica Iranica, Mar. 16, 2013, vol. 51, No. 2, pp. 125-128.
Forward, K.R. et al. "A comparison between the Strep A Rapid Test Device and conventional culture for the diagnosis of streptococcal pharyngitis", Can. J. Infect. Dis. Med. Microbiol., Jul./Aug. 2006, vol. 17, No. 4, pp. 221-223.
Joshi, D. et al. "Diagnostic accuracy of urinary reagent strip to determine cerebrospinal fluid chemistry and cellularity", Journal of Neuroscience in Rural Practice, Apr.-Jun. 2013, vol. 4, Issue 2, pp. 140-145.
Kelly, E.G. et al. "Leucocyte esterase in the rapid diagnosis of pediatric septic arthritis", Medical Hypotheses, Feb. 2013, vol. 80, No. 2, pp. 191-193.
Maltezou, H.C. et al. "Evaluation of rapid antigen detection test in the diagnosis of streptococcal pharyngitis in children and its impact on antibiotic prescription", Journal of Antimicrobial Chemotherapy, Dec. 2008, advance access publication Sep. 11, 2008, vol. 62, pp. 1407-1412.
Nibhanipudi, K.V. "Usefulness of Leukocyte Esterase Test Versus Rapid Strep Test for Diagnosis of Acute Strep Pharyngitis", Global Pediatric Health, Jan.-Dec. 2015, pp. 1-5.
Pelucchi, C. et al. "Guideline for the management of acute sore throat" Journal of Clin.Microbiology and Infection, Apr. 18, 2012, Supplement 1, pp. 1-27.
Shaikh, N. et al. "Accuracy and Precision of the Signs and Symptoms of Streptoccal Pharyngitis in Children: A Systematic Review", The Journal of Pediatrics, Mar. 2012, vol. 160, No. 3, pp. 487-493.

* cited by examiner

*Primary Examiner* — Ralph Gitomer
(74) *Attorney, Agent, or Firm* — Winthrop & Weinstine, P.A.

(57) ABSTRACT

The present invention relates to the field of infectious diseases. The invention specifically relates to the diagnostic test for acute bacterial pharyngitis. The test is used in screening for Group A Beta Haemolytic *Streptococcus* by the identifying the presence of leukocyte esterase in the throat. The Leukocyte Esterase Throat Swab Test is compared to the Rapid Step Test for efficiency in terms of fast delivery of results.

6 Claims, 1 Drawing Sheet

LEUKOCYTE ESTERASE DETECTION FROM THROAT SWAB

CROSS REFERENCE TO RELATED APPLICATIONS

This application claims priority to Indian Patent Application No. 33/CHE/2015, filed Jan. 2, 2015, the content of which is incorporated by reference herein in its entirety.

FIELD OF INVENTION

The present invention relates diagnostic aid in the field of infectious diseases. The invention specifically relates to the diagnostic test for acute bacterial pharyngitis. The test is used in screening for Group A Beta Haemolytic *Streptococcus* by the identifying the presence of leukocyte esterase in the throat.

BACKGROUND OF INVENTION

Pharyngitis is the inflammation of the pharynx, a region in the back of the throat. In most cases it is quite painful, and it is the most common cause of a sore throat. Most of the acute cases are caused by viral infections (40-80%), with the remainder being caused by bacterial infections, fungal infections, or irritants such as pollutants or chemical substances.

Amongst the bacterial organisms that cause the acute pharyngitis, the most common are Group A beta-haemolytic Streptococci. The other types of bacteria causing this disease are non-Group A beta-haemolytic streptococci and *Fusobacterium*, though less common.

The bacterial pharyngitis caused by streptococci will be called streptococcal pharyngitis here onwards. The typical symptoms of streptococcal pharyngitis are soar throat, fever with temperature above 38° C., tonsillar exudates, and enlarged tender cervical lymph nodes. The minor symptoms could be headache, nausea, vomiting, abdominal pain, muscle ache, scarlantiniform rash and petechiae on the palate. It is contagious by means of contact.

Though symptoms like red eyes, hoarseness, runny nose or mouth ulcers are the first leads for the diagnosis of streptococcal pharyngitis, they are not conclusive, more so in the absence of fever. The confirmatory tests can be either throat culture or the Rapid Strep Test. Throat culture involves taking a swab of the infected area or the exudates and culturing the sample on a suitable culture medium. This test is more reliable, specific for Group A beta-haemolytic Streptococci with high sensitivity and is affordable. The Rapid Strep test or Rapid Antigen Detection Test works by detecting the presence of GAS (Group A Streptococci) in the throat of a patient by responding to GAS-specific antigens on a throat swab. When the sample is applied on an antigen incorporated film strip, it changes color if the test is positive. It gives the results within several minutes.

There is a downside to both these testing procedures. In case of the throat culture, the results take at least 48 hours to be revealed and a culture requires special facilities. This will delay the administration of necessary medication given to the patient that will avoid further complications like the rheumatic fever, and local suppurative complications. In the case of Rapid Strep Test, the downside is the high cost of the film strips that contain the antibodies for GAS antigen incorporated in them. Although, rapid strep test cannot distinguish GAS infection from asymptomatic carriage of the said organism, it is sufficient to provide immediate symptomatic treatment.

In an article published by Shaikh et al. in *Pediatrics* 2012 March, 160(3): 487-493, titled '*Accuracy and Precision of the Signs & Symptoms of Strep. Pharyngitis in children—a Systematic Review*', it was stated that no individual symptoms or signs were effective in confirming streptococcal pharyngitis. It was suggested that the symptoms and signs, either individually or combined into predictive indicators, cannot be used to definitely diagnose or rule out streptococcal pharyngitis.

In another article published by Maltezou H C et al. in *J. Antimicrob. Chemother.* 2008 December 62(6):1407-12 dol: 1093/jac/dkn376.Epub 2008 Sep. 11, titled '*Evaluation of rapid antigen detection test in the diagnosis of streptococcal pharyngitis in children and its impact on antibiotic prescription*', the usefulness of Rapid Antigen Detection Test (RADT) in the diagnosis of streptococcal pharyngitis in children and its impact on antibiotic prescription was stated to be studied and that it was found that RADT provided appropriate guidance to treat strep throat infections and reduce the need for unnecessary cultures and usage of antibiotics.

In an article published by Forward K V et al. in *Canadian J. Infect. dis. Med. Microbiology* 2006, July 17(4)221-3, titled '*A comparison between the strep A Rapid Test device and conventional culture for the diagnosis of strep A Pharyngitis*', stated that it was found that in cases of strep pharyngitis the rapid strep test has a sensitivity of only 72%.

In the *Text book of Pediatrics,* 13th edition—Streptococci pages 577-578, authored by Richard Behrman et al., the lesions caused by the streptococcal pharyngitis were described to be characterized by edema, hyperemia and infiltration of polymorphonuclear leukocytes.

Joshi D et al. have disclosed in their article titled '*Diagnostic accuracy of reagent strip to determine CSF chemistry & cellularity*' published in *J. Neuroscience Rural Practice* 2013 April 4(2):140-5. Dol:10 4103/0976-3147.112737, the usage of urine reagent strip for semi-quantitative assessment of protein, glucose and presence of LE in CSF thus, suggesting that the existing reagent strip can be used to diagnose meningitis in low resource settings.

Farahmed. F et al. disclosed in their publication titled '*Diagnosis of spontaneous bacterial peritonitis in children by reagent strip*' in *Actamed Iran,* 20B, March 16; 51(2): 125-8, their study on the effectiveness of dipstick (LE & nitrite) for diagnosis of bacterial peritonitis in cirrhotic patients. It was found that the sensitivity, specificity, positive and negative predictive value of LE reagent might prove as a rapid bedside diagnostic test for diagnosis of spontaneous bacterial peritonitis in cirrhotic patients.

Kelly and her colleagues, according to their article titled '*LE in rapid diagnosis of pediatric septic arthritis and found that LE test is very useful for rapid diagnosis of septic arthritis*' published in *Med Hypothesis* 2013, February 80(2):19-3 dol 10 1016/May 2012 11026 EPub 2012 Dec. 19, studied the usage of LE in rapid diagnosis of septic arthritis and found that LE test is very useful for rapid diagnosis of septic arthritis.

The ESCMID Sore throat Guideline Group consisting of Pelucchi. C et al., in their article titled '*Guideline for the management of acute sore throat*' published in *J. Clin. Microbiol. Infect.* 2012 Apr. 18, supplement 1:1-28, dol: 10.1111/j.1469-0691.2012.03766, outlined the guidelines to diagnose and treat patients with a strep throat. It was suggested that the Centor Scoring should be used along with Rapid Antigen Test, and recommended that antibiotics may not be used for Centor Scores of 0-2 as suppurative complications were infrequent with these scores.

From an extensive study and understanding of the prior art, it was found that the throat culture, though the best and specific method, is a very slow process to confirm the streptococcal infection. The Rapid Strep Test presents an alternative to the throat culture for rapid results which can be an important strategy to reduce unnecessary antibiotic use or the delay in the treatment, thus avoiding further complications. However, this test can be costly and may not be affordable in low resource settings.

It was also found in the prior art that early polymorphonuclear leukocyte response in the pharyngo-tonsilar region which results in the release of leukocyte esterase in the lesions in the throat is caused by the streptococcal pharyngitis.

The present invention presents a possible alternative method to the Rapid Strep Test that can be performed at a lower cost but with equal efficiency to the Rapid Strep Test in terms of fast delivery of results. The present invention is based on the fact that the *streptococcus pharyngitis* causes lesions that result in the release of leukocyte esterase.

OBJECTIVE OF THE INVENTION

The objective of the present invention is to provide a method of diagnostic test for screening for a bacterial source in acute bacterial pharyngitis infection.

Another objective of the present invention is to provide a method of applying the Leukocyte Esterase Test to screen for a bacterial source of infection in acute bacterial pharyngitis.

Yet another objective of the present invention is to show that the efficiency of the Leukocyte Esterase Test is equal to the Rapid Strep Test for a bacterial source of infection in acute bacterial pharyngitis.

It is also the objective of the present invention to show that the Leukocyte Esterase Test is more cost-effective than the Rapid Strep Test.

SUMMARY OF THE INVENTION

The present invention relates to a method of diagnostic test using the Leukocyte Esterase swab to screen for a bacterial source of infection in acute bacterial pharyngitis and also to show the similarity in the efficiency of this test to that of Rapid Strep Test in terms of fast delivery of results.

One embodiment of the present invention relates to a method of diagnostic test to screen for a bacterial source of infection in acute bacterial pharyngitis.

One embodiment of the present invention relates to a method of diagnostic test to screen for a bacterial source of infection in acute bacterial pharyngitis using the Leukocyte Esterase Test.

Another embodiment of the present invention relates to a method of diagnostic test to screen for a bacterial source of infection in acute bacterial pharyngitis using the Leukocyte Esterase Test from a throat swab sample.

Another embodiment of the present invention relates to a method of diagnostic test to screen for a bacterial source of infection in acute bacterial pharyngitis using the Leukocyte Esterase Test from a throat swab sample with a multi-stick test strip.

Another embodiment of the present invention relates to a method of diagnostic test to screen for a bacterial source of infection in acute bacterial pharyngitis using the Leukocyte Esterase Test from a throat swab sample with a multi-stick test strip which consists of a leukocyte area specific for granulocyte esterase.

Another embodiment of the present invention relates to a method of diagnostic test to screen for a bacterial source of infection in acute bacterial pharyngitis using the Leukocyte Esterase Test from a throat swab sample with a multi-stick test strip which consists of a leukocyte area specific for granulocyte esterase, comprising of the following steps:
  i. Checking for preliminary clinical symptoms of acute bacterial pharyngitis
  ii. Collecting the sample from the throat with a swab
  iii. Smearing the swab on the multi-stick test strip
  iv. Observing for any color change.

Another embodiment of the present invention relates to a method of diagnostic test to screen for a bacterial source of infection in acute bacterial pharyngitis using the Leukocyte Esterase Test from a throat swab sample with a multi-stick test strip which consists of a leukocyte area specific for granulocyte esterase, comprising of the following steps:
  i. Checking for preliminary clinical symptoms of acute bacterial pharyngitis such as soar throat, fever, erythema of pharynx, tonsils, exudates
  ii. Collecting the sample from the pharyngo-tonsillar region of the throat with a swab
  iii. Smearing the swab on the leukocyte testing area which is specific for granulocyte esterase of the multi-stick test strip
  iv. Observing for any color change to purple color.

Another embodiment of the present invention relates to a method of diagnostic test to screen for a bacterial source of infection in acute bacterial pharyngitis using the Leukocyte Esterase Test from a throat swab sample with a multi-stick test strip which consists of a leukocyte area comprising of the following steps:
  i. Checking for preliminary clinical symptoms of acute bacterial pharyngitis such as soar throat, fever, erythema of pharynx, tonsils, exudates
  ii. Collecting the sample from the pharyngo-tonsillar region of the throat with a swab
  iii. Smearing the swab on the leukocyte esterase testing area which is specific for granulocyte esterase of the multi-stick test strip
  iv. Observing for a color change to purple color wherein, the sensitivity of the test is equal to or more than 15 wbcs/micromol$^3$.

Another embodiment of the present invention relates to a method of diagnostic test to screen for a bacterial source of infection followed by confirming the cause as Group A beta-haemolytic streptococcal infection in acute bacterial pharyngitis.

Another embodiment of the present invention relates to a method of diagnostic test to screen for a bacterial source of infection using the Leukocyte Esterase Test followed by confirming the cause as Group A beta-haemolytic streptococcal infection with a throat culture of the throat sample.

Yet another embodiment of the present invention discloses that the Leukocyte Esterase Throat Swab Test is as efficient as Rapid Strep Test in terms of fast delivery of results.

Yet another embodiment of the present invention discloses that the cost-effectiveness of the Leukocyte Esterase Throat Swab Test is more than the Rapid Strep Test.

DETAILED DESCRIPTION OF THE INVENTION

Figure 1:
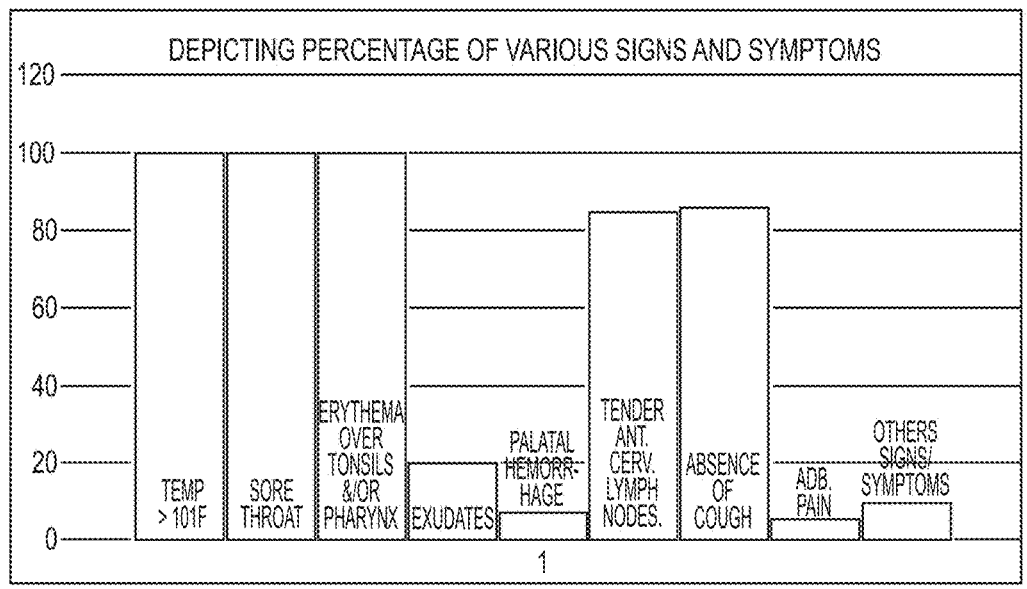
FIG. 1: shows a graph drawn depicting the percentages of various signs and symptoms identified in acute bacterial pharyngitis.
Figure 2:
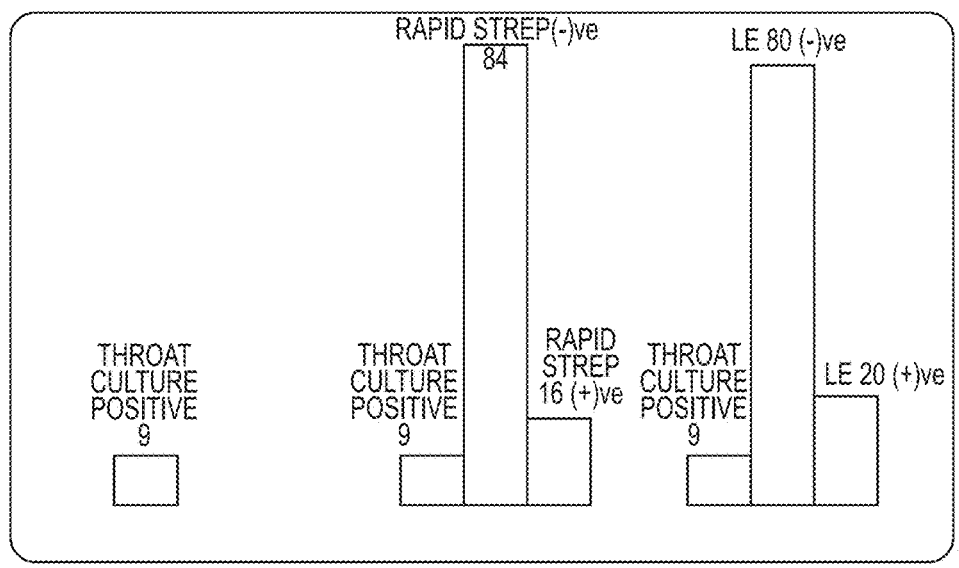
FIG. 2: shows a graph drawn depicting comparative study of the results of leukocyte esterase throat swab test and rapid strep test.

The present invention discloses a method of diagnostic test for the screening for a bacterial source of infection in acute bacterial pharyngitis using the Leukocyte Esterase Test from a throat swab sample with a multi-stick test strip which consists of a leukocyte area specific for granulocyte esterase.

In one embodiment of the present invention the method of performing the test for the screening for a bacterial source of infection in acute bacterial pharyngitis using the Leukocyte Esterase Test from a throat swab sample with a multi-stick test strip which consists of a leukocyte area specific for granulocyte esterase is described in the following steps:
 i. Checking for clinical symptoms of acute bacterial pharyngitis such as soar throat, fever, erythema of pharynx, tonsils, exudates
 ii. Collecting the sample from the pharyngo-tonsillar region of the throat with a swab
 iii. Smearing the swab on the leukocyte esterase testing area which is specific for granulocyte esterase of the multi-stick test strip
 iv. Observing for a color change to purple color.

In another embodiment of the present invention the sensitivity of the Leukocyte Esterase Test from a throat swab sample with a multi-stick test strip is equal to or more than 15 wbcs/micromol$^3$.

In yet another embodiment of the present invention, the experimental procedure for comparing the efficiency of the Leukocyte Esterase Test from a throat swab sample with a multi-stick test strip to that of the efficiency of the Rapid Strep Test was described comprising of the following steps:

A) Selection of Symptoms:

The symptoms presented basic grounds for selection of the subjects. These symptoms can range from soar throat and fever as the preliminary complaints to clinically diagnosed symptoms like erythema of pharynx, tonsils, exudates, erythema of tonsils, tender anterior cervical lymph nodes, absence of cough, petechiae/haemorrhages over the palate, abdominal pain, vomiting and skin rash.

B) Selection of Subjects:

There were 100 subjects enrolled in total each of who was of age less than 15. All the subjects showed at least three of the symptoms listed above. The percentage of signs and symptoms observed in the subjects is depicted in the table below:

TABLE 1

| No. of Subjec-ts | Fever | Sore Throa-t | Eryt-hema Over tonsils &/or Phar-ynx | Exu-date-s | Palat-al Hem-orrha-ge | Tende-r Ant. Cerv. Lymp-h Nodes | Absen-c-e Of Cough | Abd. Pain | Other signs/sy-mptoms like skin rash, Vomitin-g |
|---|---|---|---|---|---|---|---|---|---|
| 100 | 100 | 100 | 100 | 20 | 8 | 85 | 86 | 6 | 10 |

C) Selection of Multi-Stick Test Strip:

The multi-stick test strip is structured such that it consists of a leukocyte area onto which the throat swab sample is applied. The presence of granulocyte esterases is revealed by change of color to purple color. The esterase cleaves a derevitalized pyrazole amino acid ester to liberate derevitalized hydroxyl pyrazole. This pyrazole then reacts with diazonium salt to produce a purple color.

D) Testing Procedure:

The test procedure can be explained in the following steps:
 i. All the patients were first checked for the presence of signs and symptoms listed above.
 ii. An informed consent was taken from the parents of the subjects, the subjects themselves being children. The assent of the subjects was also taken.
 iii. Three swabs of the sample were collected from the pharyngo-tonsilar region of the throat of the subjects.
 iv. The first swab was used for culturing the sample collected, the second swab was used for the Rapid Strep Test, and the third swab was used for the Leukocyte Esterase Test.

E) Precautions Taken During the Test:

There were some precautions taken during the test to maximize the accuracy of the tests. None of the patients were given any antibiotic on the first day till the culture reports were obtained. Instead, they were asked to use saline gargles and analgesics. None of the patients developed any suppurative complications like peritonsilar abscess. Also the test procedure was approved by the IRB and was performed with informed consent of the parents.

F) Results:

The results obtained of the tests for screening for a bacterial source of infection in acute bacterial pharyngitis are described below:
 i. 84 out of the 100 Rapid Strep Tests done were negative.
 ii. 16 out of the 100 Rapid Strep Tests were positive.
 iii. 80 out of the 100 Leukocyte Esterase Tests were negative.
 iv. 20 out of the 100 Leukocyte Esterase Tests were positive.
 v. 9 out of the 100 cultures were positive for Group A beta-haemolytic *streptococcus*.
 vi. 9 out of the 16 positive Rapid Strep Tests were confirmed by the throat culture test.
 vii. 9 out of the 20 positive Leukocyte Esterase Tests were confirmed by the throat culture test.
 viii. Further, it was noticed that 7 out of the 20 subjects who had exudates showed throat culture positive for *streptococcus*.
 ix. Further, 6 out of the 8 subjects who had palatal haemorrhages showed throat culture positive for *streptococcus*.

G) Centor Criteria:

The modified Centor Criteria was used for the experimental procedure of the present invention for the evaluation and management of *streptococcus* pharyngitis. The Centor criteria method involves assignment of one point to each criterion to decide the treatment mode of the effected subjects. The criteria are:
 i. Absence of cough
 ii. Swollen and tender cervical lymph nodes.
 iii. Temperature above 38° C.

iv. Tonsilar exudate or swelling
v. Age less than 15 years (3 to 14 years).

Any subject positive for throat culture and satisfying the criteria was recalled back for treatment with antibiotics.

The results disclosed above have been tabulated in Table 2 as follows:

TABLE 2

| THROAT CULTURES | RAPID STREP TEST | LEUKOCYTE ESTERASE TEST |
|---|---|---|
| 9 positives | 16 (+)ve | 20 (+)ve |
| 91 negatives | 84 (−)ve | 80 (−)ve |

H) Analysis of Results:

Chi-Square 2×2 method with two tailed p-value calculations and 3×2 Fisher's Exact Test with one tailed p-value calculations were used for the analysis of the results obtained for both the Rapid Strep Test and the Leukocyte Esterase Test. The result of the analysis is disclosed in Table 3 below:

TABLE 3

| | RAPID STREP TEST | LEUKOCYTE ESTERASE TEST |
|---|---|---|
| Two tailed p-value | 0.0012 | 0.0047 |
| One tailed p-value | <0.0001 | <0.0001 |

The sensitivities of the three tests have also been disclosed to be
 Throat culture: sensitivity is 100% whereas specificity is 100% with a positive predictive value of 100% and a negative predictive value of 100%.
 Rapid strep test: sensitivity is 100% whereas specificity is 92.31% with a positive predictive value of 56.25% and a negative predictive value of 100%.
 LE test-throat: sensitivity is 100% whereas specificity is 87.91% with a positive predictive value of 45% and a negative predictive value of 100%.

I) Comparison of Prices:

A comparison of the prices of the Rapid Strep Test and the Leukocyte Esterase Test was done and it was found that the Rapid Strep Test strip was approximately 4 to 5$ each while the Leukocyte Esterase Test multi-stick test strip was less than 10 cents each.

J) Conclusions:

From the results of the experimental studies to compare the Rapid Strep Test and the Leukocyte Esterase Test described above, it was concluded that:

i. The time taken for obtaining the results of Leukocyte esterase test is almost same as that of the rapid strep test which is about a few minutes.
ii. The Leukocyte Esterase Test from a throat swab sample with a multi-stick test strip is as efficient as the Rapid Strep Test in terms of fast delivery of results.
iii. The cost of a Leukocyte Esterase Test multi-stick test strip is much less than a Rapid Strep Test strip.
iv. The cost-effectiveness of the Leukocyte Esterase Test is better than the Rapid Strep Test.
v. Hence it can be concluded that the usefulness of the Leukocyte Esterase Test from a throat swab sample with a multi-stick test strip is equal to, if not better than the Rapid Strep Test in screening for bacterial infections causing acute pharyngitis in children.

I claim:

1. A method of testing a patient for a Group A beta-haemolytic streptococcal infection, comprising:
   swabbing a throat of the patient;
   performing a test for the infection of the throat using a Leukocyte Esterase Test;
   diagnosing the patient as having or not having the infection.

2. The method of claim 1, wherein the Leukocyte Esterase Test is a multi-stick test strip.

3. The method of claim 2, wherein the multi-stick test strip consists of a leukocyte area specific for granulocyte esterase.

4. The method of claim 3, further comprising of the following steps:
   Checking for preliminary clinical symptoms of acute bacterial pharyngitis
   Smearing the swab on the multi-stick test strip
   Observing for any color change.

5. The method of claim 4, wherein:
   checking for preliminary clinical symptoms of acute bacterial pharyngitis includes checking for sore throat, fever, erythema of pharynx, tonsils, or exudates;
   collecting the sample from the throat with a swab includes collecting the sample from the pharyngo tonsillar region;
   smearing the swab on the multi-stick test strip includes smearing the swab on the leukocyte testing area which is specific for granulocyte esterase; and
   observing for any color change includes observing for any color change to purple color.

6. The method of claim 5, wherein, the sensitivity of the test is equal to or more than 15 wbcs/micromol$^3$.

* * * * *